United States Patent

Brady et al.

Patent Number: 5,133,746
Date of Patent: Jul. 28, 1992

[54] INTRAOCULAR LENS WITH ROUGHENED FIXATION MEMBER

[75] Inventors: Daniel G. Brady, Mission Viejo; Stanley Van Gent, Elk Grove; David A. Fencil, Goleta, all of Calif.

[73] Assignee: Allergan, Inc., Irvine, Calif.

[21] Appl. No.: 628,381

[22] Filed: Dec. 14, 1990

Related U.S. Application Data

[60] Continuation-in-part of Ser. No. 430,875, Nov. 2, 1989, Pat. No. 4,978,354, which is a division of Ser. No. 228,955, Aug. 4, 1988, Pat. No. 4,888,013, which is a division of Ser. No. 96,745, Sep. 15, 1987, Pat. No. 4,790,846, which is a continuation of Ser. No. 806,376, Dec. 9, 1985, abandoned.

[51] Int. Cl.⁵ .......................... A61F 2/16; B29D 11/00
[52] U.S. Cl. .......................... 623/6; 623/901; 264/1.7; 156/182; 156/293; 156/305
[58] Field of Search .......................... 623/6, 901, 18, 22; 264/1.1, 1.7; 156/182, 293, 303.1, 305

[56] References Cited

U.S. PATENT DOCUMENTS

| | | | |
|---|---|---|---|
| 3,512,184 | 5/1970 | Grove | 623/22 |
| 3,938,198 | 2/1976 | Kahn et al. | 623/22 |
| 4,242,761 | 1/1981 | Chase et al. | 623/6 |
| 4,668,446 | 5/1987 | Kaplan et al. | 623/6 X |
| 4,737,322 | 4/1988 | Bruns et al. | 623/6 X |

FOREIGN PATENT DOCUMENTS

| | | | |
|---|---|---|---|
| 0208546 | 1/1987 | European Pat. Off. | 623/6 |
| 0227357 | 7/1987 | European Pat. Off. | 623/6 |

*Primary Examiner*—Ronald Frinks
*Attorney, Agent, or Firm*—Gordon L. Peterson

[57] ABSTRACT

An intraocular lens comprising at least one fixation member and an optic. The fixation member has an attachment region with a roughened outer surface. The attachment region is received within the optic to attach the fixation member to the optic. The roughened outer surface improves the adhesion of the fixation member to the optic.

37 Claims, 2 Drawing Sheets

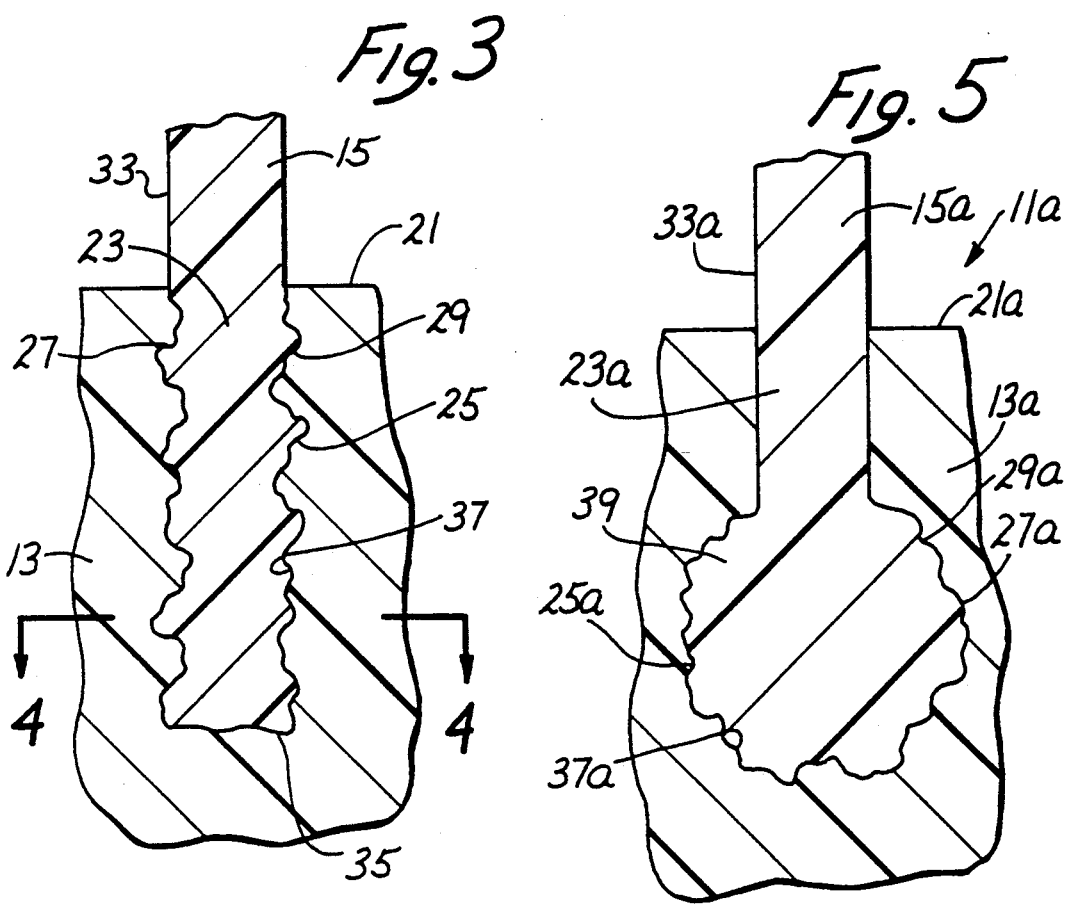
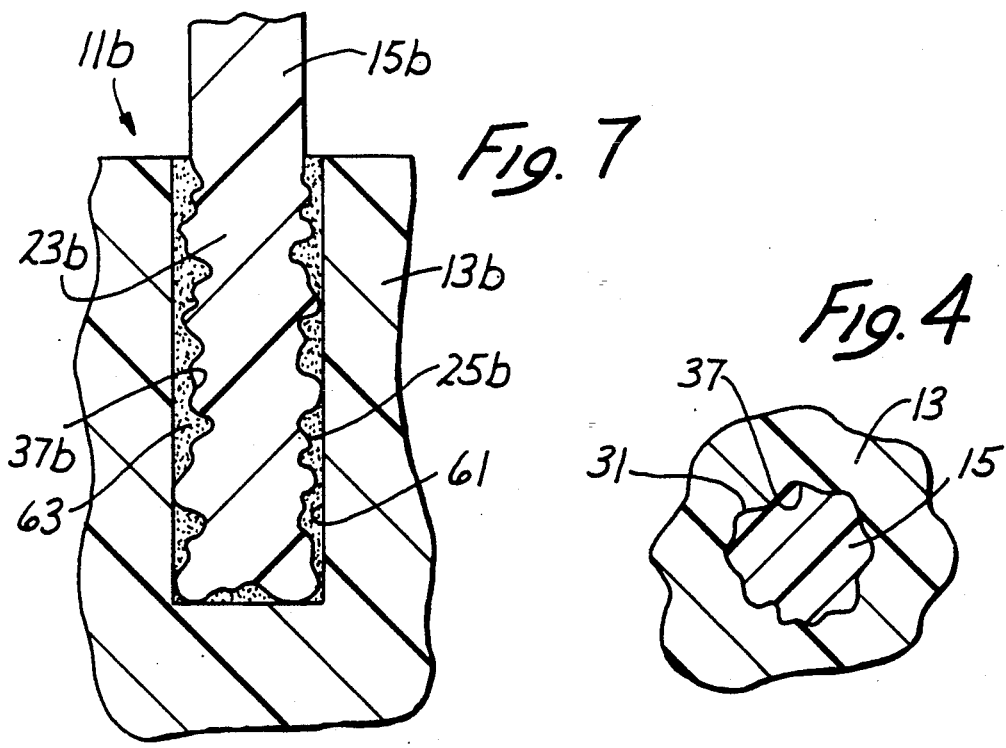

INTRAOCULAR LENS WITH ROUGHENED FIXATION MEMBER

This application is a continuation in part of application Ser. No. 430,875 filed on Nov. 2, 1989 now U.S. Pat. No. 4,978,354 which is a division of application Ser. No. 228,955 filed Aug. 4, 1988 now U.S. Pat. No. 4,888,013, which is a division of Ser. No. 096,745 filed Sept. 15, 1987 now U.S. Pat. No. 4,790,846, which is a continuation of patent application Ser. No. 806,376 filed Dec. 9, 1985, now abandoned.

FIELD OF THE INVENTION

This invention relates to intraocular lenses comprising at least one fixation member and an optic and, more particularly, to the attachment of the fixation member to the optic.

BACKGROUND OF THE INVENTION

Intraocular lenses (IOL's) are a well-known type of surgical implant used to replace the natural lens of an eye which has been damaged as a result of trauma or disease. Such IOL's typically comprise an optic and at least one fixation member attached to the optic. The fixation member functions to position the optic in the correct optical alignment within the eye. Many fixation members are of filamentary form, and are attached to the optic at or near the periphery of the optic.

It is conventional practice to construct the optic of a hard biocompatible polymer, such as polymethylmethacrylate (PMMA). More recently, it has been proposed to construct the optic from a relatively flexible or deformable material. When so constructed, the optic can be rolled or flexed into a relatively small cross-sectional configuration to permit it to be inserted through a relatively small incision into the eye to thereby reduce trauma and the likelihood of infection from the surgery.

The fixation members are constructed of a resilient material, typically polypropylene. In some IOL's, the fixation members are integrally formed with the optic. In other types of IOL's, various methods of attaching the fixation members to the optic have been devised.

The attachment of the fixation members to the optic is particularly troublesome when the optic is constructed of soft or deformable material, such as silicone. For example, when the deformable optic is folded or rolled prior to insertion through the incision into the eye, flexure of the optic creates a likelihood that the fixation members will become detached from the optic. Also, forces on the fixation members resulting from insertion of the IOL through the incision or from pulling on the fixation members to adjust the IOL after insertion, creates a likelihood that the fixation members will become detached from the optic. If this occurs, it not only renders the IOL useless, but also is a potential hazard to the patient. The soft optic materials, such as silicone, do not have sufficient rigidity to be used an integral fixation member or haptic.

SUMMARY OF THE INVENTION

This invention improves the attachment of a fixation member to an optic by roughening a surface of an attachment region, such as a proximal end portion, of the fixation member. The roughened surface is located within the optic and cooperates with the optic to attach the fixation member to the optic. Although the use of a roughened surface on the fixation member is particularly adapted for use with a flexible or deformable optic, it may also be used with a hard optic.

The roughened surface typically is, or includes, an outer peripheral surface of the attachment region. The attachment region may be any region of the fixation member which it is desired to strongly attach to the optic. Physically, the roughened surface has integral peaks and valleys which provide surface variations or irregularities and a varying perimeter. Preferably, although not necessarily, both of these variations are random. Viewed from a different perspective, the roughened surface has a stucco-like finish.

So that the roughened surface will be effective in providing a strong attachment between the fixation member and the optic, the optic has an inner surface which receives and cooperates with the roughened outer surface. Preferably, the inner surface has a shape at least partially complementary to the roughened configuration of the fixation member. Thus, the optic has peaks which project into the valleys of the roughened surface and valleys for receiving the peaks of the roughened surface. In other words, the roughened surface of the fixation member is received in an at least partly complementary mating roughened surface of the optic, and by so doing, a multiplicity of mechanical interlocks are formed which strongly attach the fixation member to the optic. Preferably, the roughened surfaces are essentially complementary and essentially mate with each other.

The inner surface of the optic can be formed in different ways. For example, it may be provided by an adhesive which strongly bonds to the main body of the optic and which conforms to the irregularities of the outer roughened surface to provide a correspondingly roughened inner surface on the optic. Although the adhesive may be considered as a separate element, it can also be considered as being a portion of the optic. Alternatively, the adhesive can be eliminated, and the main body of the optic can provide the inner surface of the optic.

The roughened surface of the fixation member should be roughened sufficiently to provide adequate pull strength when used with a flexible optic. Specifically, the roughening should provide for a pull strength of at least about 40 grams with a flexible optic. This can be accomplished in different ways.

In a quantitative sense, the roughened surface should have a surface finish at least as rough as about 60 RMS. Generally, a surface smoother than 60 RMS would not be expected to provide the necessary pull strength for a flexible optic. Preferably, the surface finish is at least as rough as 80 RMS.

The maximum desired roughness can be expressed as a function of the maximum and minimum perimeters of the roughened surface. In this regard, the maximum perimeter is preferably no more than about 2.0 times the minimum perimeter of the roughened surface. In the case of a rounded fixation member, the maximum circumference is preferably no more than about 2.0 times the minimum circumference of the roughened surface. If the maximum perimeter is more than 2.0 times the minimum perimeter, the resulting reduced minimum perimeter dimension may unacceptably weaken the fixation member.

In a preferred construction, the proximal end portion of the fixation member includes a filament, and the filament has a nominal perimeter. The roughened surface has variations in the perimeter which are no more than about plus or minus 30 percent of the nominal perimeter.

A sufficient area of the outer surface should be roughened to provide the desired pull strength. Because of the extremely small dimensions of the fixation 10 member and optic it is desirable, particularly for flexible optics, to roughen the maximum allowable roughened surface area of the proximal end portion of the fixation member. In this regard, the roughened surface is preferably roughened around its entire perimeter and for a length equal to, or slightly less than, the length of the proximal end portion which is received in the optic. This provides for a maximum strength attachment and does not subject the exposed surfaces of the fixation member to roughening as this may be undesirable when implanted in the human eye.

The roughened attachment region can be of any desired configuration. For example, the fixation member may be in the form of a cylindrical filament, and the roughened surface may be the roughened surface of the proximal end portion of the filament. Alternatively, a proximal end portion of the filament may be enlarged, either integrally or by the attachment of an anchor, and the enlargement and/or anchor may be roughened.

The inner surface of the optic, which receives the roughened outer surface of the fixation member, can be provided in different ways. For example, the optic can be formed about the attachment region of the fixation member. This may be accomplished in a variety of ways, including for example, insert molding in a process in which the optic is molded about the proximal end portion of the fixation member. Alternatively, known techniques can be employed for forming a swellable optic about the the fixation member. Another preferred technique includes forming a bore in the main body of the optic and using an adhesive between the roughened outer surface and the optic so that the adhesive forms about the roughened outer surface and provides a correspondingly roughened inner surface for the optic.

The invention, together with additional features and advantages thereof, may best be understood by reference to the following description taken in connection with the accompanying illustrative drawing.

BRIEF DESCRIPTION OF THE DRAWING

FIG. 3 is an enlarged, fragmentary sectional view illustrating the region of the fixation member which is attached to the optic.

FIG. 4 is a sectional view taken generally along line 4—4 of FIG. 3.

FIG. 5 is a fragmentary, sectional view similar to FIG. 3 illustrating a second embodiment of the invention.

FIG. 7 is a fragmentary, sectional view similar to FIG. 3 illustrating a third embodiment of the invention.

DESCRIPTION OF THE PREFERRED EMBODIMENT

Figure 1:
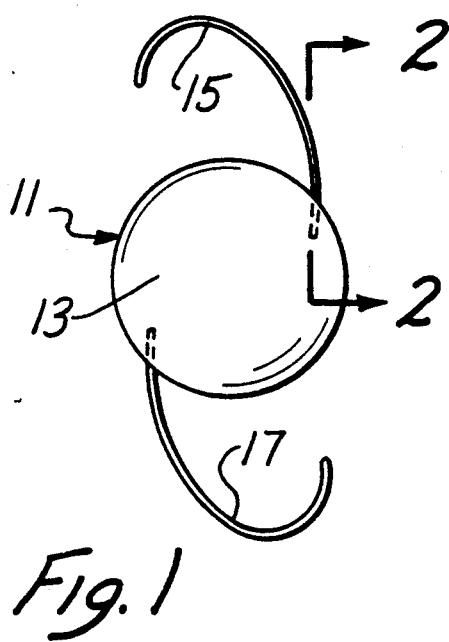
FIG. 1 is a front elevational view of an IOL constructed in accordance with the teachings of this invention.
Figure 2:
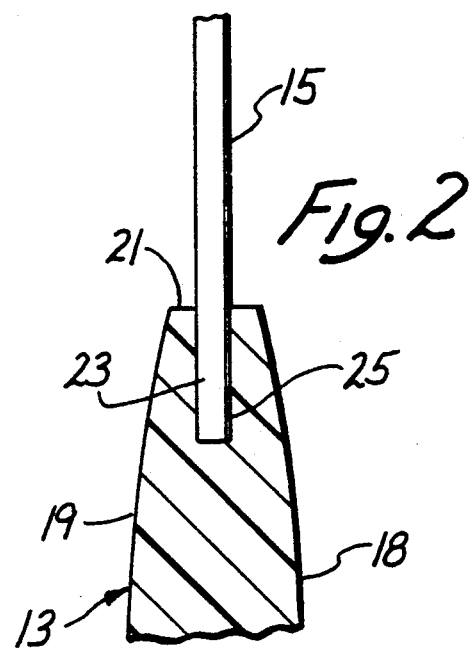
FIG. 2 is an enlarged, fragmentary sectional view taken generally along line 2—2 of FIG. 1.

FIG. 1 shows an IOL 11 which comprises an optic 13 of a transparent, biocompatible material and fixation members 15 and 17. Although the optic 13 could be of various different configurations, in the embodiment illustrated, it has a convex anterior face 18 (FIG. 2), a convex posterior face 19, and a cylindrical periphery or edge 21. The optic 13 may be constructed of any hard or soft material suitable for use in an optic. For example, the optic may be constructed of a relatively hard material, such as PMMA, or soft, deformable materials, such as silicone and polyurethane, which permit the optic 13 to be rolled or folded into a smaller configuration for insertion through a relatively small incision into the eye.

The fixation members 15 and 17 retain or fix the optic 13 in the correct position within the eye. Each of the fixation members 15 and 17 is in the form of an elongated, resilient strand or filament. Although the fixation members can be of various different configurations, in this embodiment, they are each of a generally J-shaped configuration, and they are constructed of a resilient, biocompatible material, such as PMMA or polypropylene.

The fixation member 15 has an attachment region which in this embodiment is a proximal end portion 23 of the fixation member and which is embedded within a peripheral region of the optic 13. The proximal end portion 23 has a roughened outer surface 25. In this embodiment, the roughened surface 25 has randomly located integral peaks 27 (FIG. 3) and valleys 29 which provide the desired roughness. The peaks 27 and the valleys 29 provide surface variations or irregularities and also provide the proximal end portion 23 with a randomly varying perimeter 31 (FIG. 4).

The surface finish of the roughened surface 25 is at least as rough as about 60 RMS and preferably at least as rough as 80 RMS. The maximum perimeter of the roughened surface 25 is no more than about 2.0 times the minimum perimeter of the roughened surface 25. More specifically, the fixation member 15, which is in the form of a filament, has a smooth cylindrical surface 33 (FIG. 3) which extends from the optic periphery 21. The perimeter of the cylindrical surface 33 defines a nominal perimeter or circumference of the fixation member 15. The roughened surface 25 has variations in its perimeter which are no more than about plus or minus 30 percent of the nominal perimeter, i.e., the perimeter of the cylindrical surface 33. In other words, if the nominal perimeter is considered as 1, the minimum perimeter would be no smaller than 0.7 and the maximum perimeter no larger than 1.3. In this embodiment, all of the surface area of the fixation member 15 that is embedded in the optic 13 is roughened. The surface variations along an inner end surface 35 of the fixation member 15 are optional, but if they are employed, they are preferably randomly located and sized in accordance with the surface variations of the roughened surface 25.

The roughened surface 25 may be roughened in any suitable manner, such as by sanding, sandblasting, abrading, grinding, chemically etching etc. Before roughening, the full length of the fixation member 15 has a smooth cylindrical surface, i.e., the cylindrical surface 33, extending for the full length of the fixation member. However, the roughening process converts the originally smooth, cylindrical surface into the roughened surface. As such, the peaks 27 and the valleys 29 are all integrally formed from parent material of the fixation member 15 such that the fixation member 15 remains a one-piece, integral member.

The optic 13 receives the proximal end portion 23 of the fixation member 15 and cooperates with the roughened outer surface 25 to securely attach the fixation member to the optic. In a preferred construction, this cooperation includes the optic having a roughened inner surface 37 circumscribing and receiving the roughened surface of the fixation member. The roughened surfaces 25 and 37 are essentially mating or complementary so that they can form a mechanical interlock to aid retention of the fixation member in the optic. Specifically, the surface 37 has peaks which are received in the valleys 29 and valleys which receive the peaks 27.

To obtain the essentially mating, roughened surfaces, the roughened surface 25 can be used to form the roughened inner surface 37 of the optic 13. This can be accomplished by forming of the optic about the proximal end portion of the fixation member so as to form a mechanical interlock between the roughened surfaces 25 and 37 to at least assist in attaching the fixation member to the optic. This can be accomplished, for example, by insert molding as shown, for example, in FIG. 6 or by otherwise forming of the optic about the proximal end portion 23. Of course, either or both of the fixation members 15 and 17 can be attached to the optic 13 as described above.

In the embodiment of FIGS. 1-4, an otherwise smooth cylindrical surface is roughened to provide the roughened outer surface 25. However, surfaces of various different shapes can be roughened utilizing the principles of this invention. This is illustrated by way of example in FIGS. 5 and 6 which show an IOL 11a which is identical to the IOL 11 in all respects not shown or described herein. Portions of the IOL 11a corresponding to the IOL 11 are designated by corresponding reference numerals followed by the letter "a." The primary difference between the IOL's 11 and 11a is that the latter has fixation members 15a and 17a with enlargements 39 having roughened outer surfaces 25a which have been roughened as described above in connection with FIGS. 1-3.

More specifically, the optic 13a is cast about the proximal end portion 23a to securely attach the fixation member 15a to the optic 13a. The bulbous enlargement 39 cooperates with the optic 13a to form a mechanical interlock which strongly interlocks the fixation member 15a to the optic so that rolling, folding or flexing of the optic 13a (when it is constructed of resilient, deformable materials) will not bring about detachment of the fixation member from the optic. Because the optic 13a is cast about the proximal end portion 23a of the fixation member 15a, there are no cavities or openings in the optic as a result of the attachment of the fixation member to the optic. Of course, conventional manipulation apertures may be provided in the optic 13a, if desired. The fixation member 17a (FIG. 6) is identical, in the illustrated embodiment, to the fixation member 15a and is identically attached to the optic 13a at a diametrically opposed location on the optic as shown in FIG. 1 for the IOL 11.

The enlargement 39 has a cross-sectional area which is larger than that of the remainder of the proximal end portion 23a. The material of the optic 13a intimately contacts all surfaces of the proximal end portion 23a of the fixation member so the fixation member is firmly embedded in the optic.

The fixation member 15a and the proximal end portion 23a thereof are initially in a cylindrical configuration. A region of the proximal end portion 23a can be most easily permanently deformed into a second or interlocking configuration, i.e., the enlargement 39, which is wider than the original cylindrical configuration, by heating the proximal end portion 23a, or a region thereof, to a temperature sufficient to cause it to flow to form the bulbous-shaped enlargement 39. This may be accomplished, for example, by a small flame or a $CO_2$ or Nd.:YAG laser. After heating, the molten thermoplastic material is cooled to solidify it. The enlargement 39 is formed before the optic 13a is cast about the proximal end portion 23a. If desired, the enlargement 39 may have its outer surface roughened to improve adhesion of the material of the optic 13a. In this embodiment, the enlargement 39 has its outer surface 25a roughened as described above in connection with the embodiment of FIGS. 1-4. If desired, in this embodiment the surface irregularities on the enlargement 39 may be larger than that described above in connection with FIGS. 1-4; however, preferably the surface variations in the perimeter are no more than about plus or minus 30 percent of the nominal perimeter defined by the cylindrical surface 33a.

Figure 6:
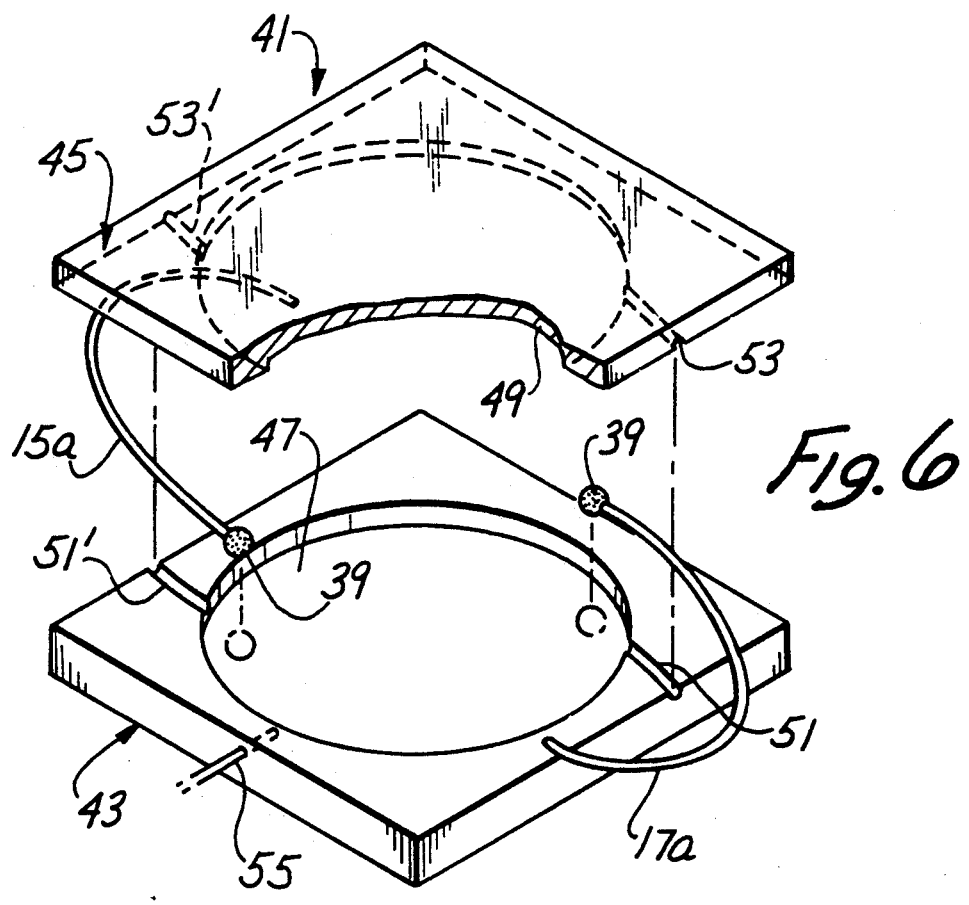
FIG. 6 is an exploded isometric view of a portion of a mold and fixation members, with the mold being shown somewhat diagrammatically.

FIG. 6 shows a mold 41 of the type which may be used for insert molding of the optic about the fixation members 15, 17 or 15a, 17a. The mold 41 of FIG. 6 is shown for use in molding the IOL 11a. The mold 41 includes a bottom mold half 43 and a top mold half 45. The mold halves 43 and 45 include mold cavities 47 and 49, respectively, whose surfaces correspond to the anterior and posterior faces of the optic to be molded. The perimeter edges of the mold cavities 47 and 49 are aligned with one another, and the parting line thus formed extends along the cylindrical edge 21a of the optic 13a. A slot 51 runs from the side of the mold half 43 and intersects the perimeter edge of the cavity 47. Another slot 53 in the mold half 45 matches with the slot 51 and similarly intersects its corresponding mold cavity 47. As the fixation member 17a which is to be positioned in slots 51 and 53 is generally cylindrical in cross section, each of the slots 51 and 53 approximates a hemicylinder or a rectangular channel. Where other fixation member configurations are contemplated, the shape or shapes of the slots 51 and 53 should be such as to hold the fixation member in proper position while minimizing leakage of the molding material and the formation of flash resulting from such leakage. Corresponding slots 51' and 53' are provided in the mold halves 43 and 45, respectively, for the fixation member 15a. While the mold 41 is shown as capable of molding and assembling a single IOL, the principles of this invention can be applied to operations which mold a plurality of IOL's simultaneously.

In operation, fixation members 15a and 17a, complete with the proper-sized enlargements 39 on their proximal end portions, are positioned in alignment with slots 51', 53' and 51 and 53, respectively. The mold halves 43 and 45 are closed. The selected optical material is injected into the closed cavity via a sprew hole 55 using conventional injection molding or casting techniques. The material is permitted to cure by chemical reaction, and then the mold halves 43 and 45 are opened to provide a completed molded and assembled IOL which requires only minimal deflashing. Separate adhesives and/or adhesive characteristics of certain materials could be used to augment the attachment between fixation members 15 and 17 and the optic 13 and the fixation members 15a and 17a and the optic 13a.

FIG. 7 shows an IOL 11b, which is identical to the IOL 11 in all respects not shown or described herein. Portions of the IOL 11b corresponding to portions of the IOL 11 are designated by corresponding reference numerals followed by the letter "b."

The primary difference between the IOL 11b and the IOL 11 is that, with the latter, an adhesive is used to form the inner roughened surface 37b of the optic 13b. More specifically, the optic 13b has a smooth wall socket 61 formed therein and an adhesive 63 in the socket. The adhesive 63, which forms a strong mechanical and/or chemical bond with the optic 13b, completely surrounds and conforms to the irregularities of the roughened outer surface 25b to thereby provide a complementary, mating roughened inner surface 37b. The adhesive 63 can be considered as part of the optic 13b. The socket 61 can be formed in different ways, such as by cutting or molding.

The adhesive 63 should form a strong enough bond with the optic 13b so as to provide the desired pull strength. Accordingly, the adhesive 63 is preferably of the type that forms a very strong bond with the smooth-walled socket 61, and a chemical bond is preferred. For example, if the optic 13b is constructed of a soft, flexible silicone material, the adhesive 63 is also preferably of a compatible kind of silicone that will readily bond to the optic. The roughened surfaces 25b and 37b are then relied upon to provide a bond of the desired strength between the adhesive and the fixation member 15b, even though the fixation member 15b is of a different kind of material, e.g. PMMA or polypropylene, from the optic 13b. In this manner, the adhesive strongly bonds to one of the components, i.e., the optic 13b and forms numerous strong mechanical interlocks with another member of dissimilar material, i.e., the fixation member 15b.

Pull strength is the tensile force required to pull the fixation member out of the optic. The desired pull strength of at least about 40 grams can be provided in different ways. When using the embodiment of FIG. 7 with a flexible optic, it is important to employ an adhesive with sufficient strength and/or wettability, and this is illustrated by the following examples:

EXAMPLE 1

Three fixation members of extruded PMMA and three additional fixation members of polypropylene were roughened in accordance with the teachings of this invention using sandpaper. Smooth-walled sockets were formed in six flexible optics of SLM-1 silicone material utilizing a 25-gauge needle. SLM-1 is crosslinked polydimethylsiloxane. This material is reinforced with silicone resin and is produced by platinum catalyzed addition curing. An SLM-1 adhesive, which is uncured SLM-1 material with no UV absorber, was provided around the roughened attachment regions of the fixation members, and the six fixation members were inserted into the sockets of the six flexible optics, respectively. The adhesive was allowed to cure for one hour at 60 degrees C to form a chemical bond with the optics. Thereafter, when subjecting these six samples to a standard pull strength test, samples using extruded PMMA fixation members exhibited pull strengths of 23, 34 and 29 grams, respectively, and the three samples using polypropylene fixation members exhibited pull strengths of 36, 32 and 29 grams, respectively.

EXAMPLE 2

Example 1 was repeated utilizing SLM-2 silicone material for the optic and SLM-2 adhesive. SLM-2 is crosslinked polydimethyldiphenylsiloxane. This material is reinforced with fumed silica and is produced by platinum catalyzed addition curing. This material is more fully described in application Ser. No. 562,452 filed Aug. 1, 1990, entitled Optically Clear Reinforced Silicone Elastomers Of High Optical Refractive Index And Improved Mechanical Properties For Use In Intraocular Lenses. SLM-2 adhesive is uncured SLM-2 material with no UV absorber. A chemical bond between the adhesive and the optics was formed. The pull strengths for the samples utilizing extruded PMMA fixation members were 56, and 49 grams, respectively, and the pull strengths for the samples utilizing polypropylene fixation members were 58, 49 and 49 grams, respectively.

Although exemplary embodiments of the invention have been shown and described, many changes, modifications and substitutions may be made by one having ordinary skill in the art without necessarily departing from the spirit and scope of this invention.

We claim:

1. An intraocular lens comprising:
    at least one fixation member having a proximal end portion, said proximal end portion having an outer surface;
    the outer surface of the proximal end portion being roughened;
    an optic, said proximal end portion being within the optic to attach the fixation member to the optic, said roughened outer surface improving adhesion of the fixation member to the optic; and
    the proximal end portion including a filament, a region of the filament having an enlargement and said roughened outer surface is on the enlargement.

2. An intraocular lens as defined in claim 1 wherein the outer surface of said enlargement is rounded.

3. An intraocular lens as defined in claim 1 wherein the enlargement includes a bulbous configuration and the roughened outer surface is on the bulbous configuration.

4. An intraocular lens a defined in claim 1 wherein the optic i flexible.

5. An intraocular lens as defined in claim 1 wherein the material of the optic intimately contacts the outer surface so that the fixation member is firmly embedded in the optic.

6. An intraocular lens as defined in claim 1 wherein the optic is flexible and an adhesive is used to augment the attachment between the fixation member and the optic.

7. An intraocular lens comprising:
    at least one fixation member having an attachment region;
    said attachment region having a roughened outer surface;
    a flexible optic having an inner surface receiving the attachment region of the fixation member and cooperating with the roughened outer surface to attach the fixation member to the optic to provide a pull strength of at least about 40 grams; and
    the optic being formed about the attachment region.

8. An intraocular lens as defined in claim 7 wherein the roughened surface has surface irregularities which are randomly located on the attachment region.

9. An intraocular lens as defined in claim 7 wherein the roughened surface has surface variations which cause the perimeter of the roughened surface to vary randomly.

10. An intraocular lens as defined in claim 7 wherein the roughened surface has a stucco-like finish.

11. An intraocular lens as defined in claim 7 wherein the attachment region includes a filament having a nominal perimeter and the roughened surface has variations in the perimeter which are no more than about plus or minus 30 percent of the nominal perimeter.

12. An intraocular lens as defined in claim 7 wherein the inner surface of the optic is roughened, said roughened surfaces at least partially mating with each other.

13. An intraocular lens as defined in claim 7 wherein the optic is cast about said attachment region.

14. An intraocular lens comprising:
  at least one fixation member having an attachment region;
  said attachment region having a roughened outer surface, said roughened outer surface having randomly located surface irregularities and a randomly varying perimeter; and
  a flexible optic receiving the attachment region of the fixation member and cooperating with the roughened outer surface to attach the fixation member to the optic.

15. An intraocular lens as defined in claim 14 wherein the attachment region includes a filament having a nominal perimeter and the roughened outer surface has irregularities in the perimeter which are no more than about plus or minus 30 percent of the nominal perimeter.

16. An intraocular lens as defined in claim 14 wherein the optic has a roughened surface receiving the roughened outer surface of the fixation member, said roughened surfaces essentially mating with each other.

17. An intraocular lens comprising:
  at least one fixation member having an attachment region;
  said attachment region having a roughened outer surface, said roughened outer surface having a stuccolike finish; and
  a flexible optic receiving the attachment region of the fixation member and cooperating with the roughened outer surface to attach the fixation member to the optic.

18. An intraocular lens as defined in claim 17 wherein the attachment region includes a filament having a nominal perimeter and the roughened outer surface has variations in the perimeter which are no more than about plus or minus 30 percent of the nominal perimeter.

19. An intraocular lens as defined in claim 17 wherein the optic has a roughened inner surface receiving the roughened outer surface of the fixation member, said roughened surfaces essentially mating with each other.

20. An intraocular lens as defined in claim 17 including an adhesive defining a roughened inner surface of the optic which receives the roughened outer surface of the fixation member.

21. An intraocular lens comprising:
  at least one fixation member having an attachment region;
  said attachment region having a roughened outer surface with a surface finish at least as rough as about 60 RMS, said roughened outer surface having a varying perimeter along its length and a maximum perimeter which is no more than about 2.0 times a minimum perimeter of the roughened outer surface; and
  an optic having an inner surface receiving the attachment region of the fixation member and cooperating with the roughened outer surface to attach the fixation member to the optic.

22. An intraocular lens as defined in claim 21 wherein the attachment region includes a filament having a nominal perimeter and the roughened surface has variations in the perimeter which are no more than about plus or minus 30 percent of the nominal perimeter.

23. An intraocular lens as defined in claim 21 wherein the roughened surface has surface variations which are randomly located on the attachment region.

24. An intraocular lens as defined in claim 21 wherein the roughened surface has surface variations which cause the perimeter of the roughened surface to vary randomly.

25. An intraocular lens as defined in claim 21 wherein the roughened surface has a stucco-like finish.

26. An intraocular lens as defined in claim 21 wherein the optic is flexible.

27. An intraocular lens as defined in claim 24 wherein the optic is flexible and includes an adhesive defining said inner surface, said inner surface being roughened and mating with the roughened outer surface.

28. An intraocular lens as defined in claim 21 wherein the inner surface of the optic is a roughened surface and receives the roughened outer surface of the fixation member, said roughened surfaces being essentially complementary.

29. An intraocular lens as defined in claim 21 including an adhesive defining said inner surface.

30. A method of making an intraocular lens comprising:
  providing at least one fixation member with the fixation member having an attachment region and with the attachment region having a roughened outer surface; and
  forming an optic about the attachment region of the fixation member to form a mechanical interlock between the roughened outer surface and the optic and to at least assist in attaching the fixation member to the optic.

31. A method as defined in claim 30 wherein the step of providing includes sanding the attachment region to form the roughened outer surface.

32. A method as defined in claim 30 wherein the step of providing includes abrading the attachment region to form the roughened outer surface.

33. A method as defined in claim 30 wherein the step of forming includes forming a flexible optic about the attachment region of the fixation member.

34. A method as defined in claim 30 wherein the step of forming includes molding an optic about the attachment region of the fixation member.

35. A method of making an intraocular lens comprising:
  inserting a roughened attachment region of a fixation member into a socket of a flexible optic, said socket having a wall; and
  adhering the roughened attachment region of the fixation member to the wall of the socket with an adhesive.

36. An intraocular lens comprising:
  at least one fixation member having an attachment region;

said attachment region having a roughened outer surface;
a flexible optic having a socket opening at a surface of the optic and receiving the attachment region of the fixation member; and an adhesive in the socket adhering the attachment region of the fixation member to the optic.

37. An intraocular lens as defined in claim 36 wherein the socket has a smooth wall.

* * * * *

UNITED STATES PATENT AND TRADEMARK OFFICE
CERTIFICATE OF CORRECTION

PATENT NO.   :   5,133,746
DATED        :   July 28, 1992
INVENTOR(S)  :   Daniel G. Brady et al It is certified that error appears in the above—identified patent and that said Letters Patent is hereby corrected as shown below:

Column 3, line 5, after "fixation" delete "10".

Column 8, line 16, after "56," add -- 44 -- .

Column 8, line 45, change "a defined" to -- as defined -- .

Column 8, line 46, change "i flexible" to -- is flexible -- .

Signed and Sealed this

Nineteenth Day of October, 1993

Attest:

BRUCE LEHMAN

Attesting Officer

Commissioner of Patents and Trademarks